United States Patent [19]

Lunn

[11] 4,450,270
[45] May 22, 1984

[54] DIOXIMINO CEPHALOSPORIN ANTIBIOTICS

[75] Inventor: William H. W. Lunn, Indianapolis, Ind.

[73] Assignee: Eli Lilly and Company, Indianapolis, Ind.

[21] Appl. No.: 500,729

[22] Filed: Jun. 3, 1983

Related U.S. Application Data

[62] Division of Ser. No. 307,983, Oct. 2, 1981, Pat. No. 4,402,955.

[51] Int. Cl.³ .................. C07D 501/38; A61K 31/545
[52] U.S. Cl. ........................................ 544/24; 544/25; 544/21; 424/246
[58] Field of Search .................... 424/246; 544/24, 25, 544/21, 26, 22

[56] References Cited

U.S. PATENT DOCUMENTS

| | | | |
|---|---|---|---|
| 4,200,575 | 4/1980 | Numata et al. | 424/246 |
| 4,258,041 | 3/1981 | O'Callaghan et al. | 424/246 |
| 4,267,176 | 5/1981 | Kamiya et al. | 424/246 |
| 4,278,671 | 7/1981 | Ochiai et al. | 424/246 |
| 4,336,253 | 6/1982 | Lunn et al. | 544/25 |
| 4,402,955 | 9/1983 | Lunn | 544/25 |

OTHER PUBLICATIONS

Derwent Abstract 32890, 0/19.
Nomura et al., Jour. of Med. Chem. vol. 17, No. 12, pp. 1312–1315 (1974).

*Primary Examiner*—Nicholas S. Rizzo
*Attorney, Agent, or Firm*—William B. Scanlon; Arthur R. Whale

[57] ABSTRACT

Broad spectrum cephalosporin betaine antibiotics represented by the formula

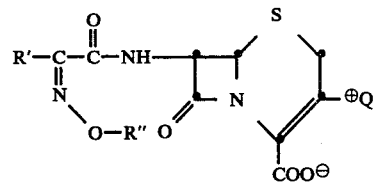

wherein Q is an oximino-substituted pyridinium, quinolinium or isoquinolinium group of the formulas

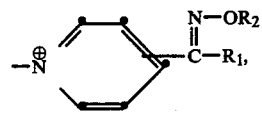

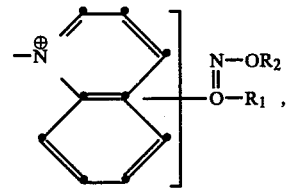

or

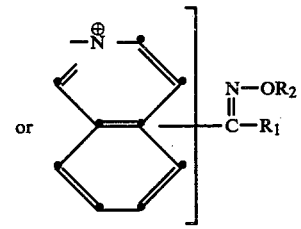

wherein $R_1$ and $R_2$ are hydrogen or $C_1-C_3$ alkyl; and R' is an amino-substituted 5- or 6-membered heterocyclic, e.g., 2-aminothiazol-4-yl; and R" is $C_1-C_4$ alkyl, an N-substituted carbamoyl group, or a carboxy-substituted alkyl or cycloalkyl group; have potent activity vs. G⁻ organisms. Pharmaceutical formulations and a method for treating infectious disease with above compounds are provided.

3 Claims, No Drawings

DIOXIMINO CEPHALOSPORIN ANTIBIOTICS

This application is a division, of application Ser. No. 307,983, filed Oct. 2, 1981 now U.S. Pat. No. 4,602,955.

BACKGROUND OF THE INVENTION

This invention relates to semi-synthetic cephalosporin antibiotics. In particular, it relates to cephalosporin compounds wherein the cephalosporin bicyclic nucleus is substituted in the 3'-position by an oxime-substituted pyridinium, quinolinium, or isoquinolinium group and in the 7-position with a 2-(amino-substituted heterocyclic)-2-oximinoacetamido group.

Cephalosporin antibiotic compounds substituted in the 3'-position with a quaternary ammonium group have been known for some time. One of the first derivatives of cephalosporin C which was prepared was cephalosporin $C_A$ (pyridine), Hale, Newton, and Abraham, Biochem. J., 79 403 (1961). Cephaloridine, the well-known clinical antibiotic, is the 3'-pyridinium cephalosporin, 7-(α-thienylacetamido)-3-(pyridinium-1-ylmethyl)-3-cephem-4-carboxylate.

Recent research has again centered on the synthesis and study of 3'-quaternary ammonium derivatives of cephalosporins. Recently, Heymes et al., U.S. Pat. No. 4,152,432, described semi-synthetic cephalosporin antibiotics wherein the 7-position side chain is a 7-[2-(2-aminothiazol-4-yl)-2-alkoxyiminoacetamido] group. 3'-Quaternary ammonium derivatives of the cephalosporins having this side chain have been described recently by Belgium Pat. No. 853,545, and more recently by O'Callaghan, et. al., in U.S. Pat. No. 4,258,041. The latter-described compounds have a carboxy-substituted branched alkyl group on the oxygen of the oxime function in the 7-position side chain.

Continual improvement is sought in antibiotic therapy to overcome deficiencies in the existing practice. The semi-synthetic cephalosporin antibiotics have long been recognized as broad spectrum antibiotics, and several have achieved clinical importance. Continued research with the cephalosporin antibiotics has, as one of its goals, the development of antibiotics having higher activity against resistant microorganisms, particularly the gram-negative microorganisms, as well as antibiotics with an even broader spectrum of activity.

SUMMARY OF THE INVENTION

This invention is concerned with broad spectrum cephalosporin antibiotics represented by the following structural formula

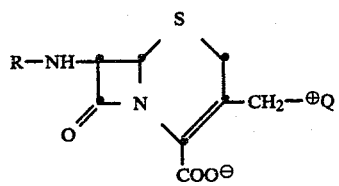

wherein R is hydrogen, formyl or a 2-(5- or 6-membered heterocyclic ring)-2-oximinoacetyl group, and ⊕Q represents an oximino-substituted pyridinium, quinolinium, and isoquinolinium group. R in the formula 1 can be for example, the 7-[2-(2-aminothiazol-4-yl)-2-methoxyiminoacetyl, the 7-[2-(2-aminopyridyl-6-yl)-2-methoxyiminoacetyl group, or the 7-[2-(5-amino-1,2,4-thiadiazol-3-yl)-2-methoxyiminoacetyl group.

The compounds of the invention are preferably prepared by the reaction of the corresponding 7-acylamido-3-iodomethyl cephalosporin with the oximino-substituted pyridine, quinoline, or isoquinoline group.

The compounds of the invention and pharmaceutical compositions comprising compounds of the invention are useful in a therapeutic method for the treatment of infectious diseases in man and animals. The compounds of the invention are broad spectrum cephalosporin antibiotics having pronounced activity against the gram-positive and gram-negative microorganisms which are pathogenic to man and animals.

DETAILED DESCRIPTION OF THE INVENTION

The cephalosporin antibiotic compounds of this invention are represented by the following structural formula 1

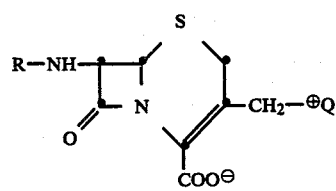

wherein R is hydrogen, formyl, or an acyl group represented by the formula

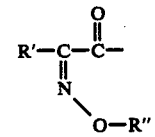

wherein R' is a 5- or 6-membered heterocyclic ring represented by the formulas

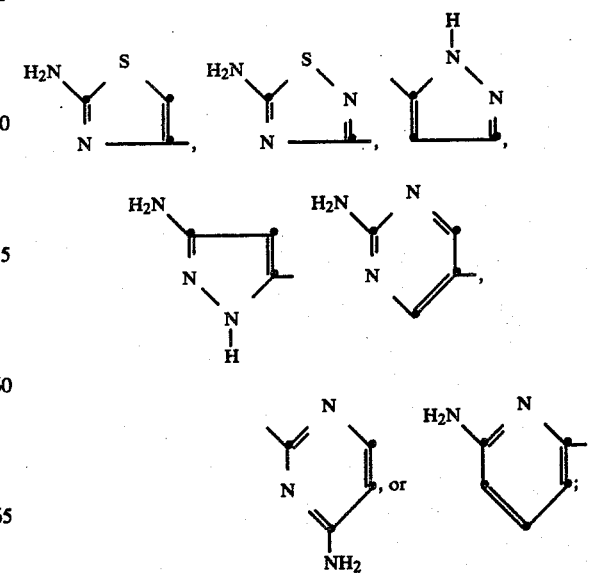

R" is hydrogen, $C_1$-$C_4$ alkyl, a carboxy-substituted alkyl or a carboxy-substituted cycloalkyl group represented by the formula

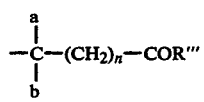

wherein a and b when taken separately are independently hydrogen or $C_1$-$C_3$ alkyl, and when taken together with the carbon atom to which they are attached form a $C_3$-$C_7$ carbocyclic ring, n is 0–3, and R''' is hydroxy, $C_1$-$C_4$ alkoxy, amino, or —OR° wherein R° is a carboxy-protecting group; or
R" is a carbamoyl group represented by the formula

wherein R"" is $C_1$-$C_4$ alkyl, phenyl, or $C_1$-$C_3$ alkyl substituted by phenyl;
Q is an oximino-substituted pyridinium, quinolinium or isoquinolinium group represented by the formulas

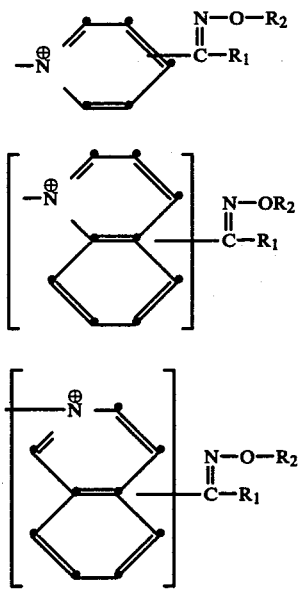

wherein $R_1$ is hydrogen or $C_1$-$C_3$ alkyl, and $R_2$ is hydrogen or $C_1$-$C_3$ alkyl; and the pharmaceutically acceptable non-toxic salts thereof.

In the above formula 1 the term $C_1$-$C_4$ alkyl refers to methyl, ethyl, n-propyl, isopropyl, n-butyl, sec-butyl, and like lower alkyl groups. The term "$C_1$-$C_3$ alkyl substituted by phenyl" refers to benzyl, phenylethyl, 3-phenylpropyl, 2-phenylpropyl, and the like. The term "$C_1$-$C_4$ alkoxy" refers herein to the lower alkyloxy radicals such as methoxy, ethoxy, n-propoxy, isopropoxy, n-butoxy, t-butoxy, and like straight and branched chained alkoxy radicals.

The term carboxy-protecting group refers to the readily removable ester groups commonly used to protect the carboxylic acid functional groups in the cephalosporin art. Such esters include the alkyl and substituted alkyl esters, for example, t-butyl, 2,2,2-trihaloethyl esters such as 2,2,2-trichloroethyl, and 2-iodoethyl; the aryl alkyl ester groups such as benzyl and substituted benzyl, for example, p-methoxybenzyl, p-nitrobenzyl, diphenylmethyl, p-methoxydiphenylmethyl, and like ester groups. The carboxy-protecting ester group, R°, functions merely to protect the carboxy group of the carboxy-substituted alkyl or cycloalkyl group attached to the oxime oxygen. As such protecting groups, they serve merely for the temporary protection of the carboxy function during the preparation of the compounds of the invention. A preferred carboxy-protecting group of this invention is the trialkylsilyl ester function, for example, the trimethylsilyl ester group. These trialkylsilyl ester protecting groups are preferred because they are most easily removed by simple hydrolysis. As described hereinafter in connection with the preferred method for preparing the compound of the invention, the silyl ester protection group is employed.

Examples of carboxy-substituted alkyl groups represented by the term R" above include those wherein R''' is hydroxy such as carboxymethyl, 2-carboxyethyl, 3-carboxypropyl, 2-carboxyprop-2-yl, 1-carboxyethyl, 2-carboxybut-2-yl, 3-carboxypent-3-yl, and like carboxy-substituted alkyl groups. Examples of carboxy-substituted cycloalkyl groups include 1-carboxycycloprop-1-yl, 1-carboxymethylcycloprop-1-yl, 1-(2-carboxyethyl)cycloprop-1-yl, 1-carboxycyclobut-1-yl, and 1-carboxycyclopent-1-yl, and like carboxy and carboxyalkyl-substituted cycloalkyl groups. Examples of carboxy-substituted alkyl and cycloalkyl groups wherein R''' is $C_1$-$C_4$ alkoxy are methoxycarbonylmethyl, ethoxycarbonylethyl, isopropoxycarbonylethyl, ethoxycarbonylethyl, methoxycarbonylbutyl, 2-ethoxycarbonylprop-2-yl, 2-t-butyloxycarbonylprop-2-yl, 1-methoxycarbonylcyclobut-1-yl, 1-ethoxycarbonylmethylcyclopent-1-yl, and like lower alkyl esters of the carboxy-substituted alkyl and $C_3$-$C_7$ carbocyclic alkyl groups. When in the above formula R''' is an $NH_2$ group, examples of such groups are provided by the amides of the abovenamed carboxy-substituted alkyl and cycloalkyl groups.

Illustrative of the examples of carbamoyl groups represented by the term R" in the above formula 1 are N-methylcarbamoyl, N-ethylcarbamoyl, N-propylcarbamoyl, N-phenylcarbamoyl, N-benzylcarbamoyl, N-phenethylcarbamoyl, and like carbamoyl groups.

The term "oximino" as used herein refers to the group

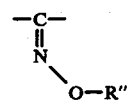

and to the

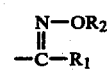

substituent group.

The compounds of the invention represented by the formula 1 wherein R is an acyl group as defined and R''' is hydroxy, $C_1$-$C_4$ alkoxy, or amino, are antibiotic compounds having activity against a broad spectrum of microorganisms including the gram-positive and gram-negative microorganisms. In particular, the 7-acyl compounds are highly active against gram-negative microorganisms such as enterobacter, salmonella, pseudomonas, serratia, klebsiella, and proteus. They also exhibit activity against the gram-positive organisms such as staphylococcus and streptococcus. The antibiotic compounds are useful in inhibiting the growth of microorganisms which are pathogenic to man and animals and are useful in a method for treating infectious diseases as described hereinafter.

The compounds represented by the formula 1 wherein R is hydrogen or formyl are useful as intermediates in the preparation of the compounds wherein R is an acyl group.

The antibiotic compounds of this invention are represented by the following formula 2

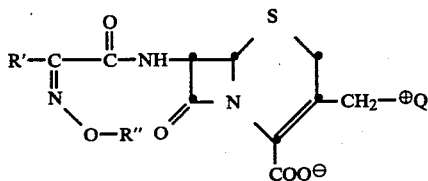

wherein R' is 2-aminothiazole-4-yl, 5-amino-1,2,4-thiadiazole-3-yl, 3-aminopyrazol-5-yl, pyrazol-5-yl, 2-aminopyrimidin-5-yl, 4-aminopyrimidin-2-yl, and 2-aminopyridin-6-yl; and R'' and $Q^{\oplus}$ have the same meanings as defined in formula 1. The compounds of the formula 2 are prepared by alternative methods. In one such method, a 3-acetoxymethyl cephalosporin having a 7-acyl group as defined in formula 1 is reacted with the oximino-substituted pyridine, quinoline, or isoquinoline, to provide a compound of the formula 2. The reaction is carried out by following procedures known in the art for the preparation of 3'-pyridinium-substituted cephalosporins. For example, the 3-acetoxymethyl cephalosporin is reacted with the oximino-substituted heterocyclic base in an aqueous reaction medium at a temperature between about 25° C. and 65° C. Aqueous media comprising a water miscible organic solvent such as acetone can be used and, in many instances, a catalytic amount of an iodide salt such as sodium iodide or potassium iodide is added to the reaction mixture to enhance the rate and yield of the reaction.

In another method for preparing the compounds of formula 2, a 3-halomethyl cephalosporin substituted in the 7-position with the same acyl group as described for formula 2 above is reacted with the oximino-substituted pyridine, quinoline, or isoquinoline to provide a compound of the invention. This method is illustrated in the following reaction scheme.

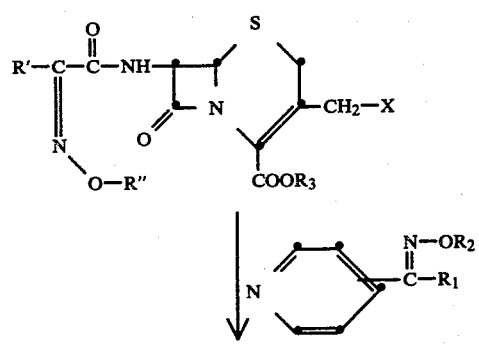

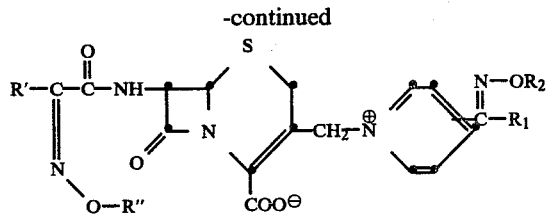

wherein X is chloro, bromo, or iodo and $R_3$ is a carboxy-protecting group. The carboxy-protecting group is preferably a trialkylsilyl group which upon hydrolysis following displacement affords the compound of formula 2 as shown above. In the case where $R_3$ is a carbon ester such as one of the carboxy-protecting groups described hereinabove for R°, the product of the displacement reaction is the betaine salt formed with the acid of the displaced halide, for example, the chloride, bromide or iodide salt. Upon removal of the carboxy-protecting group $R_3$, a compound of the invention is obtained.

In the above reaction scheme the preparation of the compounds of the formula 2 by this method is illustrated with an oximino-substituted pyridine. The oximino-substituted quinoline and isoquinoline compounds react similarly to provide the compound of the formula 2 wherein Q is the oximino-substituted quinolinium or isoquinolinium group.

The preferred method for preparing the compounds of the invention comprises the use of the starting material in the above reaction scheme wherein X is iodo. These compounds are readily prepared by the method described by Bonjouklian, U.S. Pat. No. 4,266,049, issued May 5, 1981. According to the described method, a 3-acetoxymethyl-substituted cephalosporin or an ester thereof is reacted with a trialkylsilyliodide, for example, trimethylsilyliodide (TMSI) in an inert aprotic organic solvent under anhydrous conditions to provide the corresponding 3-iodomethylcephalosporin ester. In carrying out the preparation of a compound of the formula 2, a 3-acetoxymethyl cephalosporin substituted in the 7-position with the acyl group described for formula 1 is first silylated with a silylating agent to block the $C_4$ carboxy group, and also when R'' is hydrogen or a carboxy-substituted alkyl or cycloalkyl group, the oxime hydroxy group and the carboxy group are protected as well. The amino group of the amino-substituted heterocyclic in the 7-position side chain is likewise silylated at this point in the process. The silylating reagent can be any of a number of the commonly employed silylating agents, for example, N-methyl-N-trimethylsilyltrifluoroacetamide (MSTFA), bis-trimethylsilylacetamide, and like reagents.

The silylated starting material is then reacted with a trialkylsilyliodide, for example, trimethylsilyliodide to form the silylated 3-iodomethyl derivative as represented in the above reaction scheme wherein $R_3$ is a trialkylsilyl group. Trimethylsilyliodide is the preferred trialkylsilyliodide agent. The silylated 3-iodomethyl derivative is then reacted with the oximino-substituted pyridine, quinoline, or isoquinoline to provide the compound of the formula 2 in silylated form. Upon treatment of the reaction mixture with water, the compound of the formula 2 is obtained. The above-described preferred process is illustrated by the following reaction scheme.

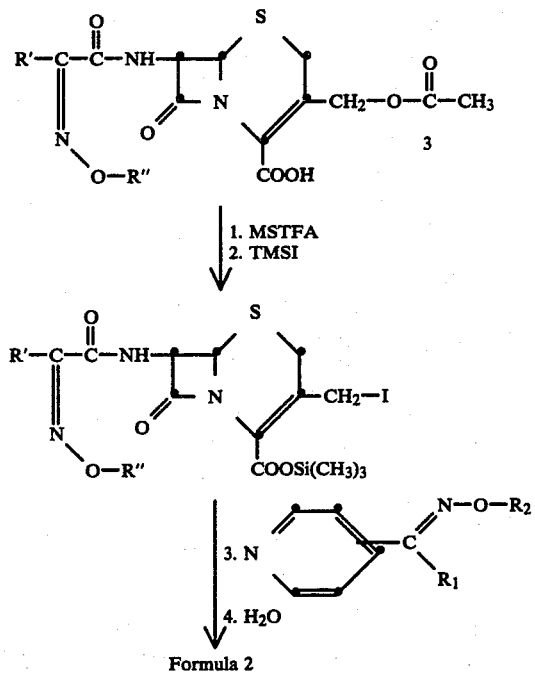

Formula 2

In an example of the preparation of the compound of the invention by the above preferred method, a suspension of 7-[2-(2-aminothiazol-4-yl)-2-methoxyiminoacetamido]-3-acetoxymethyl-3-cephem-4-carboxylate in chloroform is reacted with N-methyl-N-trimethylsilyltrifluoroacetamide at room temperature with stirring. After a complete solution is obtained, trimethylsilyliodide is added and the solution is stirred at room temperature. After between about 15 minutes and 1 hour of reaction time, the reaction mixture is evaporated to remove the solvent and the silylated 3-iodomethyl derivative is dissolved in dry acetonitrile and the solution treated with tetrahydrofuran. The treatment with tetrahydrofuran destroys any excess TMSI present in the reaction mixture. The solution is then mixed with a solution of the oximino-substituted pyridine, quinoline or isoquinoline compound in acetonitrile, and the reaction mixture is stirred at about room temperature for between 1 and 6 hours. The reaction is best run under concentrated conditions and, when complete, the reaction mixture is treated with a small amount of water sufficient to hydrolyze the silyl-blocking groups. The product being of ionic character precipitates from the non-polar reaction medium and is separated by filtration or centrifugation or other suitable means. The product at this point is generally crude and can be purified by C-18 silica reverse phase high performance liquid chromatography (HPLC) using a mixture of acetonitrile, acetic acid and water at a composition of about 10% acetonitrile, 2% acetic acid and 80% water.

The antibiotic compounds of the invention represented by the formula 2 can also be prepared by the acylation of a compound of the formula 1 wherein R is hydrogen. The 3'-substituted nucleus compounds are prepared by the reaction of 7-aminocephalosporanic acid (7-ACA) with the desired oximino-substituted pyridine, quinoline or isoquinoline. The substituted nucleus is then acylated with an oximino-substituted derivative of the desired heterocyclic acetic acid represented by the following formula.

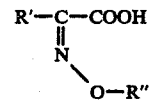

wherein R' and R'' have the same meanings as defined hereinabove. An active derivative of the oximino-carboxylic acid is used in the acylation. For example, the acid group is reacted with hydroxybenzotriazol (HBT) and a carbodiimide such as dicyclohexylcarbodiimide, and the HBT ester formed is used to acylate the 7-amino group of the substituted nucleus. Other active derivatives of the oximino-substituted carboxylic acid can be used in the acylation, for example, the acid azide, or an acid anhydride such as is formed with methyl chloroformate or isobutyl chloroformate. When in the above formula of the oximino-substituted carboxylic acid R'' is a carboxy-substituted alkyl or cycloalkyl group and R''' is hydroxy, the free carboxylic acid function represented thereby is protected by a carboxy-protecting group during the acylation. When in the above formula R'' is hydrogen, the free hydroximino group need not be protected when, for example, the acylation is carried out with an active ester such as the HBT ester.

The starting materials employed in the above-described processes are prepared by methods known in the art. For example, the 7-acylamino 3-acetoxymethyl cephalosporins represented by the above formula 3 are prepared by the acylation of 7-amino cephalosporanic acid by employing acylation methods known in the art. Heymes, et al., U.S. Pat. No. 4,152,432, described the preparation of compounds of the formula 3 wherein R' is the 2-aminothiazol-4-yl and R'' is lower alkyl. The compounds of the formula 3 wherein R' is the 2-aminopyridin-6-yl, 2-aminopyrimidin-5-yl, or 4-aminopyrimidin-2-yl, are described by U.S. Pat. No. 4,267,176. The compounds represented by the formula 3 wherein R' is 5-amino-1,2,4-thiadiazol-3-yl are described in European patent application No. 0,007,470, while the compounds represented by formula 3 wherein R' is 3-aminopyrazol-5-yl are prepared as described by U.K. Pat. No. 2,046,734A.

The compounds of the formula 1 wherein R is formyl are useful intermediates for preparing the antibiotic compounds of the invention. They can be used in a method for preparing the 7-amino-3-(oximino-substituted quaternary)-3-cephem-4-carboxylate nucleus compounds (formula 1, R=H).

According to this alternative method, N-formyl 7-aminocephalosporanic acid (7-formamidocephalosporanic acid) is converted to the silylated 3-iodomethyl derivative 7-formamido-3-iodomethyl-3-cephem-4-carboxylic acid silyl ester by the method of Bonjouklian described hereinabove. The 3-iodomethyl derivative is reacted with the oximino-substituted quinoline, isoquinoline, or pyridine to obtain a compound represented by the formula 1 wherein R is formyl. The N-formyl product is converted to the 7-amino nucleus compound (formula 1, R=H) by hydrolysis in methanolic hydrochloric acid.

The compounds of the formula 1 wherein R' is a pyrazol-5-yl or 3-aminopyrazol-5-yl group are prepared by employing methods known in the art. The 2-(pyrazol-5-yl)-2-oximinoacetic acid or the 2-(3- aminopyrazol-5-yl)-2-oximinoacetic acid is prepared and converted to an active derivative of the carboxylic acid, for example, an active ester. The active ester is coupled, via N-acylation, with 7-aminocephalosporanic acid and the 7-[2-(pyrazol-5-yl)-2-oximinoacetamido]-3-acetoxymethyl-3-cephem-4-carboxylic acid and 7-[2-(3-aminopyrazol-5-yl)-2-oximinoacetamido]-3-acetoxymethyl-3-cephem-4-carboxylic acid are converted to the corresponding 3-iodomethyl silylated derivatives as described herein. The latter are reacted with the oximino-substituted pyridine, quinoline or isoquinoline to provide the respective compound of the invention.

The pyrazole and aminopyrazole oximino substituted acetic acids are prepared by employing synthetic methods known in the art. For example, the 2-(pyrazol-5-yl)-2-alkoxyiminoacetic acid is prepared by heating in an inert hydrocarbon solvent the acetyl oximino compound of the formula A

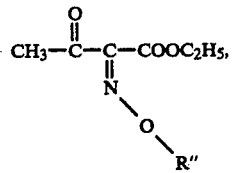

wherein R'' is other than hydrogen as defined above, with dimethylformamide dimethylacetal to form the dimethylaminomethylene oximino ester of the formula

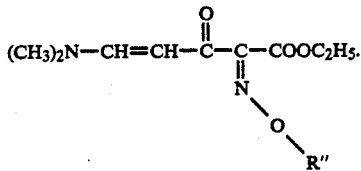

The latter is reacted with hydrazine hydrate to provide the ethyl ester of 2-(pyrazol-5-yl)-2-alkoxyiminoacetic acid. The ester is hydrolyzed to the free acid and the acid converted to an active ester for acylation.

The 2-(3-aminopyrazol-5-yl)-2-alkoxyiminoacetic acid is prepared by reacting the compound of the formula A with carbon disulfide and two equivalents of methyl iodide to form the intermediate compound of the formula B

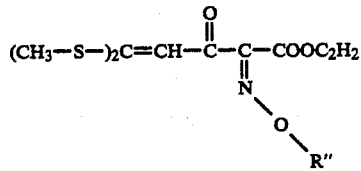

Intermediate B is reacted with N-t-BOC hydrazine to provide compound C,

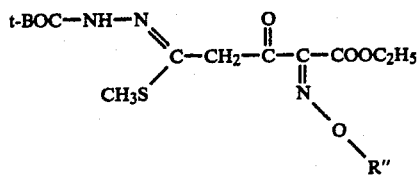

and C is reacted with hydrazine hydrate to form 2-(3-t-BOC-hydrazinopyrazol-5-yl)-2-oximinoacetic acid ethyl ester D.

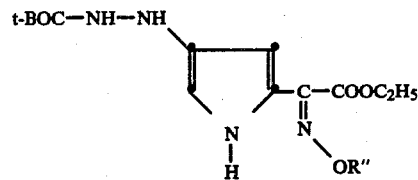

Compound D is treated in the cold with trifluoroacetic acid to remove the t-BOC group and the 3-hydrazinopyrazole is nitrosated with nitrous ($NHO_2$) acid in the cold to form 2-(3-azidopyrazol-5-yl)-2-oximinoacetic acid ethyl ester. The azido group is reduced to the amino group by chemical reduction to provide the 2-(3-aminopyrazol-5-yl)-oximinoacetic acid ethyl ester. The ester is hydrolyzed under alkaline conditions to the free acid.

The acylation procedure described in the above references for preparing the compounds of the formula 3 are acylation methods previously known in the cephalosporin art. For example, the acylation with the amino-substituted heterocyclic oximino-substituted carboxylic acid is preferably carried out with an active derivative of the carboxylic acid, for example, with an acid halide, acid azide or an active ester thereof. Active esters formed with hydroxybenzotriazole are preferred in the acylation. These acylation methods can be either aqueous or non-aqueous acylations. For example, under non-aqueous conditions 7-ACA can be converted to a silyl ester, for example, a trimethylsilylester and the ester derivative reacted in a non-aqueous medium such as acetonitrile or tetrahydrofuran with the active ester of the carboxylic acid. Under aqueous conditions, an active derivative such as an acid halide of the acylating carboxylic acid can be employed in a solvent system comprising water and a water miscible solvent such as acetone. An acid-binding agent is used to accomodate the acid formed during the coupling reaction. Acid-binding agents such as tertiary amines, for example, triethylamine or pyridine can be used as well as an inorganic base such as sodium bicarbonate or sodium carbonate. During the non-aqueous acylations, the $C_4$ carboxylic acid group of 7-ACA can be protected by silylation as mentioned above or with a conventional carboxy-protecting group such as a readily removable ester such as benzhydryl, p-nitrobenzyl, p-methoxybenzyl, and like esters. Likewise, the amino group of the amino-substituted heterocyclic ring in the 7-position side chain can be protected for purposes of the acylation. A conventional amino protecting group can be employed such as, for example, a haloacyl group such as chloroacetyl, or dichloroacetyl, an alkoxycarbonyl group or aryloxycarbonyl group, for example, t-butyloxycarbonyl, or benzyloxycarbonyl. Also, the amino group of the heterocyclic ring can be protected by silylation as, for example, with a trialkylsilyl halide in the presence of a hydrogen halide acceptor. Preferably, in non-aqueous acylations all reactive groups may be blocked by silylation prior to the acylation reaction.

Examples of oximino-substituted pyridines, quinolines and isoquinolines employed as described above in the preparation of the compounds of the invention include the following:

4-formylpyridine oxime, 4-formylpyridine methoxime, 3-formylpyridine oxime, 3-formylpyridine methoxime, 4-formylpyridine ethoxime, 3-formylpyridine n-propoxime, 2-formylpyridine oxime, 2-formylpyridine methoxime, 3-acetylpyridine oxime, 4-acetylpyridine oxime, 2-acetylpyridine oxime, 3-acetylpyridine methoxime, 3-acetylpyridine isopropoxime, 4-propionylpyridine oxime, 4-propionylpyridine methoxime, 4-butyrylpyridine oxime, 3-propionylpyridine ethoxime, 3-butyrylpyridine oxime, and like pyridine oximes; the quinoline and isoquinoline oximes such as 4-formylquinoline oxime, 4-formylisoquinoline oxime, 4-formylquinoline methoxime, 6-formylisoquinoline oxime, 4-formylquinoline methoxime, 6-formylisoquinoline methoxime, 6-formylquinoline oxime, 8-formylquinoline oxime, 8-formylisoquinoline methoxime, 6-formylisoquinoline ethoxime, 7-acetylquinoline oxime, 7-acetylquinoline n-butoxime, 5-acetylquinoline ethoxime, 6-propionylquinoline oxime, 6-propionylquinoline methoxime, 6-n-butyrylisoquinoline oxime, 5-acetylisoquinoline oxime, 5-acetylisoquinoline methoxime, 2-formylquinoline oxime, 1-formylisoquinoline methoxime, 3-formylquinoline oxime, 3-acetylquinoline oxime, 3-formylisoquinoline oxime, 3-formylisoquinoline isopropoxime, 3-acetylquinoline methoxime, and like quinoline and isoquinoline oximes.

The compounds of the invention can be characterized as betaines by virtue of the inner salt formed with the $C_4$ carboxylate anion and the positively charged quaternary nitrogen of the oxime substituted pyridinium, isoquinolinium, or quinolinium group $\oplus Q$. The compounds of the invention wherein R" is a carboxy-substituted alkyl or cycloalkyl group (R'''=OH) form salts with pharmaceutically acceptable bases, for example, alkali metal salts such as sodium and potassium, amine salts such as benzylamine, dibenzylamine, ethanolamine such as di(2-hydroxyethyl)amine, and di(3-hydroxypropyl)amine, alkylamines such as the dilower alkyl amines, for example, dimethylamine, or other desirable pharmaceutically acceptable base. Such pharmaceutically acceptable non-toxic salts are useful in the formulation and administration of the antibiotics of the invention. Likewise, the amino group of the amino-substituted heterocyclic ring in the 7-position side chain can form acid addition salts, for example, those formed with hydrochloric acid, hydrobromic acid, sulfuric acid, phosphoric acid, and the sulfonic acids, for example, methanesulfonic acid and p-toluenesulfonic acid.

Examples of compounds of the invention represented by the formula 2 are listed in the following table.

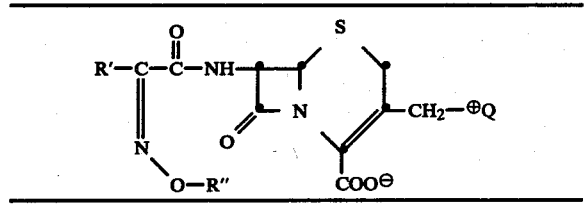

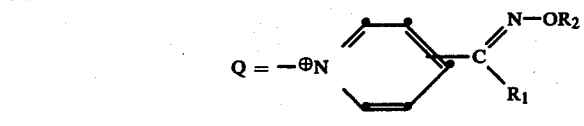

| R'¹ | R" | $R_1$ | $R_2$ | isomer |
|---|---|---|---|---|
| 2-AT | CH₃ | H | H | 3 |
| " | " | H | CH₃ | 3 |

-continued

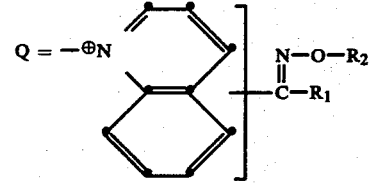

| R' | R" | $R_1$ | $R_2$ | Position |
|---|---|---|---|---|
| " | " | H | H | 4 |
| " | " | H | CH₃ | 4 |
| " | " | H | H | 2 |
| " | " | CH₃ | H | 3 |
| " | " | CH₃ | CH₃ | 3 |
| " | H | CH₃ | CH₃ | 4 |
| " | —C(CH₃)₂COOH | H | CH₃ | 3 |
| " | " | CH₃ | CH₃ | 4 |
| " | —C(O)NHCH₃ | H | CH₃ | 4 |
| " | " | C₂H₅ | H | 3 |
| " | " | CH₃ | C₂H₅ | 3 |
| " | —CH₂COOH | n-C₃H₇ | CH₃ | 4 |
| 5-ATD | CH₃ | H | H | 3 |
| " | " | H | CH₃ | 3 |
| " | " | CH₃ | C₂H₅ | 4 |
| " | H | CH₃ | CH₃ | 3 |
| " | H | CH₃ | CH₃ | 2 |
| " | H | H | H | 2 |
| " | —C(CH₃)₂COOH | H | H | 3 |
| " | " | " | " | 4 |
| " | " | CH₃ | CH₃ | 3 |
| 2-APy | CH₃ | H | H | 3 |
| " | C₂H₅ | H | CH₃ | 4 |
| " | H | CH₃ | CH₃ | 3 |
| 2-APyr. | " | H | H | 4 |
| " | CH₃ | H | CH₃ | 3 |
| " | —CH₂COOH | C₂H₅ | H | 3 |
| 4-APyr. | CH₃ | H | CH₃ | 2 |
| " | i-C₃H₇ | CH₃ | H | 3 |
| " | —C(CH₃)C(O)NH₂ | H | H | 4 |
| " | —C(CH₃)COOH | C₂H₅ | CH₃ | 3 |
| 3-APYZ | CH₃ | H | H | 4 |
| " | " | H | H | 3 |
| " | n-C₄H₉ | CH₃ | H | 2 |
| —PYZ | CH₃ | C₂H₅ | CH₃ | 3 |
| " | —OCH₂COOC₂H₅ | H | H | 3 |

| R' | R" | $R_1$ | $R_2$ | Position |
|---|---|---|---|---|
| 2-AT | CH₃ | H | H | 4 |
| " | " | H | H | 4 |
| " | " | H | CH₃ | 4 |
| " | " | H | i-C₃H₇ | 4 |
| " | C₂H₅ | CH₃ | CH₃ | 3 |
| " | CH₃ | H | H | 2 |
| 5-ATD | " | H | H | 8 |
| " | H | H | H | 4 |
| " | —C(CH₃)₂COOH | H | CH₃ | 3 |
| " | " | CH₃ | H | 4 |
| 2-APy | CH₃ | H | H | 7 |
| " | " | H | H | 4 |
| " | " | CH₃ | CH₃ | 5 |
| " | " | C₂H₅ | CH₃ | 5 |
| " | H | CH₃ | CH₃ | 8 |
| " | —C(CH₃)₂C(O)NH₂ | H | H | 8 |
| 2-APyr. | H | H | H | 2 |
| " | CH₃ | CH₃ | H | 4 |
| " | " | " | CH₃ | 5 |
| " | —C(O)NHC₂H₅ | " | H | 4 |
| " | —C(O)NHCH₃ | H | C₂H₅ | 6 |
| 4-APyr. | H | H | H | 4 |
| " | H | H | H | 5 |
| " | CH₃ | CH₃ | H | 6 |
| " | " | H | CH₃ | 5 |

-continued

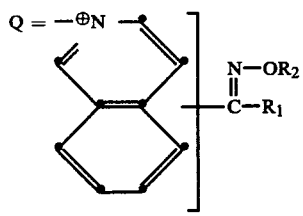

| R' | R" | R1 | R2 | Position |
|---|---|---|---|---|
|  | —CH2COOH | H | H | 3 |
| 3-APYZ | CH3 | H | H | 8 |
| " | C2H5 | H | CH3 | 5 |
| " | H | CH3 | H | 6 |
| —PYZ | —CH2CH2COOH | H | C2H5 | 5 |

$$Q = -\overset{\oplus}{N}\left[\begin{array}{c}\text{pyridinium ring with substituents}\\ N-OR_2 \\ \| \\ C-R_1\end{array}\right]$$

| R' | R" | R1 | R2 | Position |
|---|---|---|---|---|
| 2-AT | H | H | H | 3 |
| " | H | H | H | 4 |
| " | CH3 | CH3 | CH3 | 6 |
| " | —C(O)NHCH3 | " | " | 5 |
| " | —C(CH3)2COOH | " | " | 4 |
| " | —C(CH3)2C(O)NH2 | " | " | " |
| 5-ATD | H | H | H | 4 |
| " | H | H | H | 8 |
| " | CH3 | CH3 | CH3 | 4 |
| " | " | " | " | 6 |
| " | C2H5 | H | CH3 | 4 |
| " | CH3 | nC3H7 | H | 4 |
| 2-APy | H | H | H | 3 |
| " | CH3 | CH3 | CH3 | 4 |
| " | " | " | " | 7 |
| " | —C(CH3)2COONa+ | CH3 | CH3 | 5 |
| 2-APyr. | CH3 | H | H | 4 |
| " | " | CH3 | CH3 | 4 |
| " | " | H | CH3 | 5 |
| 4-APyr. | " | " | " | " |
| " | C2H5 | CH3 | CH3 | 4 |
| " | H | CH3 | H | 7 |
| 3-APYZ | " | H | H | 4 |
| " | CH3 | H | CH3 | 4 |
| " | " | CH3 | CH3 | 5 |
| " | H | H | H | 8 |
| —PYZ | —C(CH3)2COOK+ | CH3 | C2H5 | 5 |

[1] 2-AT is 2-aminothiazol-4-yl, 2-ATD is 5-amino-1,2,4-thiadiazol-3-yl, 2-APy is 2-aminopyridin-6-yl, 2-APyr is 2-aminopyrimidin-5-yl, 4-APyr is 4-aminopyrimidin-2-yl, 3-APYZ is 3-aminopyrazol-5-yl and PYZ is pyrazol-5-yl.

Preferred compounds of this invention are represented by the formula 1 wherein R' is the 2-aminothiazol-4-yl group, R" is methyl and Q is a 3- or 4-oximino-substituted pyridinium group wherein $R^1$ is hydrogen or methyl and $R^2$ is hydrogen.

The compounds of this invention preferably have the oxime function or substituted oxime function in the 7-position side chain in the syn form.

Another preferred group of compounds of this invention are represented by the structural formula 1 wherein R' is the 5-amino-1,2,4-thiadiazol-3-yl group, R" is methyl, and Q is a 3- or 4-oximino-substituted pyridinium group wherein the oximino portion $R^1$ is hydrogen or methyl and $R^2$ is hydrogen.

The antibiotic compounds of this invention represented by the formula 2 and the pharmaceutically acceptable non-toxic salts thereof are potent broad spectrum antibiotics which inhibit the growth of microorganisms pathogenic to man and animals. The compounds shown a high level of *in vitro* and *in vivo* activity against gram-negative organisms such as proteus, pseudomonas, serratia, enterobacter, and salmonella. They are also highly effective in inhibiting the growth of gram-positive microorganisms such as the staphylococci and streptococci and methicillin-resistant strains of staphylococcus.

In a further aspect of this invention, the compounds of the formula 2 and the pharmaceutically acceptable non-toxic salts thereof are provided in pharmaceutical formulations suitable for use in the treatment of infectious diseases. The formulations of this invention comprise a compound of the formula 2 and a pharmaceutical diluent. Formulations for parenteral administration comprise the antibiotic or a salt thereof at a suitable concentration in a diluent such as Water-For-Injection, 5% dextrose, physiological saline, or other pharmaceutically acceptable diluents such as Ringer's solution.

The antibiotics also can be formulated in dosage unit form comprising between about 100 mg. and 2 g. of the dry solid antibiotic in sterile vials or ampoules. The antibiotic in such dosage unit forms may be in crystalline or amorphous form. Such dosage unit forms are suitable for storage and shipment of the antibiotic and, as with other cephalosporin antibiotics, the antibiotic is dissolved in the desired diluent in the vial and the solution withdrawn by syringe for injection. Alternatively, the dosage unit formulation may be used to prepare the antibiotic in solution at a concentration between about 2% and about 20% in a pharmaceutical diluent. For example, the dosage unit form comprising 1 g. of the antibiotic or a pharmaceutically acceptable salt thereof in 10 ml. of diluent can be formulated. Another dosage unit form comprising 0.5 g./ml. is also suitable.

For administration by the intravenous route, a dosage unit form of the antibiotic may be incorporated in a physiological fluid such as one of those mentioned hereinabove. A convenient method for intravenous administration is the so-called "piggy-back" method whereby the pharmaceutical formulation of this invention is added continuously to an i.v. drip solution.

In yet a further aspect of this invention, there is provided a method for the treatment and control of infection in mammals which comprises administering to the patient an effective dose of between about 100 mg. and about 2 g. of a compound of the formula 2 or a pharmaceutically acceptable non-toxic salt thereof.

The antibiotic may be administered intramuscularly, subcutaneously, or intravenously, in a single dose or in multiple doses throughout the day. When administered i.v. the infusion method is most conveniently used. For example, a dosage unit formulation of the antibiotic is continuously mixed with a physiological fluid such as 5% dextrose and administered by the drip method.

The particular dosage and the total number of doses administered to a given patient will depend on such factors as the nature of the infection, its severity, the age and general health of the patient, as well as the tolerance of the individual patient to the antibiotic.

The following examples further illustrate the invention and the procedures by which the antibiotics thereof are prepared.

In the examples the abbreviations employed have the following meanings. HPLC is high performance liquid chromatography; MSTFA is N-methyl-N-trimethylsilyltrifluoroacetamide; TMSI is trimethylsilyliodide; THF is tetrahydrofuran; NMR is nuclear magnetic resonance spectrum; DMSO/d6 is deuterated dimethylsulfoxide; and the following letters characterizing the signals in the nmr spectrum have the following meanings; s is singlet, d is doublet, q is quartet, m is multiplet, b is broad.

The NMR spectra were run on a Jeol model No. FX-90.

EXAMPLE 1 syn-7-[2-(2-Aminothiazol-4-yl)-2-methoxyiminoacetamido]-3-[(4-formylpyridinium oxime)-1-ylmethyl]-3-cephem-4-carboxylate A suspension of 2.926 g. (6 mmole) of syn-7-[2-(2-aminothiazol-4-yl)-2-methoxyiminoacetamido]-3-acetoxymethyl-3-cephem-4-carboxylate in 12 ml. of chloroform was treated with stirring with 4.32 g. (21.6 mmole, 3.85 ml.) of N-methyl-N-trimethylsilyltrifluoroacetamide. After stirring for about one hour a complete solution was obtained and 3.24 g. (16.2 mmole, 2.29 ml.) of trimethylsilyliodide were added to the solution at room temperature. After stirring for 20 minutes, the brown reaction mixture was evaporated to remove the solvent leaving the silylated 3-iodomethyl derivative as a thick oil. The 3-iodomethyl derivative was dissolved in 8 ml. of dry acetonitrile and 648 mg. of dry tetrahydrofuran were added by pipette and the solution stirred for about 5 minutes.

One-fourth of the silylated 3-iodomethyl derivative solution (3.6 ml.) was mixed with stirring at room temperature with a solution of 238 mg. (1.95 mmole) of pyridine-4-aldoxime in acetonitrile. After stirring the reaction mixture for 2 hours water was added to the mixture. In order to maintain fluidity of the mixture an additional 4 ml. of acetonitrile were added during the addition of water. The precipitate of the title compound was separated by filtration, washed with acetonitrile and dried. There were obtained 1.033 g. of the title compound as a deep beige-colored powder. The product was purified by HPLC chromatography on a reverse phase $C_{18}$ silica column using acetonitrile/acetic acid/water, 10/2/88 percent by volume.

NMR(DMSO/d6-$D_2O$); signals at 9.33 (d, 2H), 8.40 (s, 1H), 8.20 (d, 2H), 6.71 (s, 1H), 5.64, 5.61 (d, d, 2H), 5.08, 5.04 (d, d, 2H), 3.78 (s, 3H), and 3.24 (q, 2H).

EXAMPLE 2 syn-7-[2-(2-Aminothiazol-4-yl)-2-methoxyiminoacetamido]-3-[(3-formylpyridinium oxime)-1-ylmethyl]-3-cephem-4-carboxylate By following the procedures and by using the reactants and reaction conditions described by Example 1, 3.32 g. (6.8 mmole) of syn-7-[-2-(2-aminothiazol-4-yl)-2-methoxyiminoacetamido]-3-acetoxymethyl-3-cephem-4-carboxylic acid was silylated and the silylated derivative reacted with 3.65 g. (18.25 mmol) of trimethylsilyliodide providing 15.8 ml. of a solution of the silylated 3-iodomethyl derivative in acetonitrile.

To 3.5 ml. of the above solution of the silylated 3-iodomethyl derivative was added a solution of 238 mg. (1.95 mmole) of pyridine-3-aldoxime in 1.2 ml. of dry acetonitrile (to which had been added 466 mg. (2.34 mmole) of N-methyl-N-trimethylsilyltrifluoroacetamide), and the mixture was stirred at room temperature for 2.5 hours. The reaction mixture was chilled in an ice bath and 12.6 mmole (226 μl.) of water were added by pipette. The precipitated title compound was separated by filtration and dried. There was obtained 761 mg. of the product which on purification by $C_{18}$ silica reverse phase HPLC using acetonitrile/acetic acid/water, 5/2/93 percent by volume, yielded 105 mg. of product.

NMR (DMSO/d6-$D_2O$): signals at 9.55 (bs, 1H), 9.35 (d, 1H), 8.69 (d, 1H), 8.35 (s, 1H), 8.14 (q, 1H), 6.72 (s, 1H), 5.71, 5.68 (d, d, 2H), 5.16, 5.07 (d, d, 2H), 3.79 (s, 3H), and 3.34 (q, 2H).

EXAMPLE 3 syn-7-[2-(2-Aminothiazol-4-yl)-2-methoxyiminoacetamido]-3-[(4-acetylpyridinium oxime)-1-ylmethyl]-3-cephem-4-carboxylate A. Preparation of 4-acetylpyridine oxime.

To a solution of 7.64 g. (110 mmole) of hydroxylamine hydrochloride in 150 ml. of methyl alcohol were added 5.94 g. (110 mmole) of sodium methylate and the mixture was stirred at room temperature for 10 minutes. A solution of 12.11 g. (110 mmole) of 4-acetylpyridine in 50 ml. of methyl alcohol was added dropwise over 3 minutes and the reaction mixture was stirred at room temperature for 3 hours and at the reflux temperature for 2.5 hours. After the mixture had cooled, the precipitate of sodium chloride was separated by filtration and the filtrate was concentrated by evaporation to one-half of the original volume. The concentrate was diluted with 50 ml. of water and the solution concentrated to a volume of about 100 ml. This concentrate was chilled in an ice bath for 30 minutes and the precipitate of the oxime was separated by filtration in the cold. There were obtained 8.38 g. (61.5% yield) of 4-acetylpyridine oxime.

NMR (DMSO/d6): signals at 11.65 (s, 1H), 8.66 (d, 2H), 7.61 (d, 2H), and 2.11 (s, 3H).

B. Preparation of syn-7-[2-(2-aminothiazol-4-yl)-3-methoxyiminoacetamido]-3-iodomethyl-3-cephem-4-carboxylic acid trimethylsilyl derivative.

A suspension of 7.8 g. (16 mmole) of syn-7-[2-(2-aminothiazol-4-yl)-2-methoxyiminoacetamido]-3-acetoxymethyl-3-cephem-4-carboxylic acid in 32 ml. of chloroform was silylated with 11.46 g. (57.6 mmole) of N-methyl-N-trimethylsilyltrifluoroacetamide to form a solution of the silylated derivative. To the solution were added 8.64 g. (43.2 mmole) of trimethylsilyliodide and the mixture stirred at room temperature for 30 minutes. The reaction mixture was evaporated to remove the chloroform and the silylated 3-iodomethyl derivative obtained as an oily residue was dissolved in 21 ml. of dry acetonitrile. Dry tetrahydrofuran (1.73 g., 24 mmole, 1.95 ml.) was added to the solution with stirring. The solution of the 3-iodomethyl derivative was used in the reaction described below.

C. Preparation of title compound.

A 5.4 ml. aliquot of the above solution (containing 2 mmole of the 3-iodomethyl derivative) was added to a solution of 327 mg. (2.4 mmole) of 4-acetylpyridine oxime in 1 ml. of dry acetonitrile, which has been silylated with 339 mg. (1.3 mmole) of bis-trimethylsilyltrifluoroacetamide, and the mixture was stirred at room temperature for 2.5 hours. After the reaction mixture was cooled in an ice bath, 270 mg. (15 mmole, 270 μl.) of water were added to the cold mixture by pipette. The title compound precipitated and was separated by filtration and dried. There were obtained 1.19 g. of the title compound which was purified by HPLC.

NMR (DMSO/d6-$D_2O$): signals at 9.28 (d, 2H), 8.28 (d, 2H), 6.70 (s, 1H), 5.66, 5.62 (d, d, 2H), 5.11, 5.05 (d, d, 2H), 3.75 (s, 3H), and 3.30 (q, 2H).

EXAMPLE 4 syn-7-[2-(2-Aminothiazol-4-yl)-2-methoxyiminoacetamido]-3-[(4-acetylpyridinium methoxime)-1-ylmethyl]-3-cephem-4-carboxylate A. Preparation of 4-acetylpyridine methoxime.

To a solution of 5.94 g. (110 mmole) of sodium methylate in 150 ml. of methyl alcohol was added a solution of 9.18 g. (110 mmole) of methoxylamine hydrochloride in 50 ml. of methyl alcohol. A white suspension formed and to the suspension were added 12.14 g. (110 mmole) of 4-acetylpyridine. The reaction mixture was stirred at room temperature for one hour and then filtered. The filtrate containing the product was evaporated and the residue taken up in 200 ml. of ethyl acetate. The insolubles were filtered and the filtrate evaporated into dryness. The product was obtained as the residual oil.

NMR (DMSO/d6): signals at 8.64 (d, 2H), 7.60 (d, 2H), 3.92 (s, 3H), and 2.12 (s, 3H) delta.

B. Preparation of title compound.

To a suspension of 2.73 g. (6 mmole) of syn-7-[2-(2-aminothiazol-4-yl)-2-methoxyiminoacetamido]-3-acetoxymethyl-3-cephem-4-carboxylate in 12 ml. of chloroform were added 4.30 g. (21.6 mmole) of MSTFA. After stirring at room temperature for 1.5 hours the solution of the silylated compound was treated with 3.24 g. (16.2 mmole) of TMSI and stirring was continued for 15 minutes. The reaction mixture was evaporated and the oily residue of the silylated 3-iodomethyl derivative was dissolved in 12 ml. of dry acetonitrile and the solution was treated with stirring for 15 minutes with 730 µl. of THF.

One third (6.5 ml.) of the above solution of the 3-iodomethyl derivative was added to a solution of 360.9 mg. (2.4 mmole) of 4-acetylpyridine methoxime in 1 ml. of dry acetonitrile and the mixture was stirred at room temperature for 3.5 hours. The reaction mixture was chilled and 234 µl. (13 mmole) of water were added by pipette. The crude product precipitated and was separated by filtration.

The product was purified on C-18 silica reverse phase HPLC using acetonitrile:acetic acid:water, 20%:2%:78% v:v:v. There were obtained 64 mg. of the product with the following NMR spectrum.

NMR (DMSO/d6-D2O): signals at 9.52 (d, 2H), 8.27 (d, 2H), 6.73 (s, 1H), 5.68, 5.67 (d, d, 2H), 5.11, 5.08 (d, d, 2H), 3.83 (bs, 6H), and 2.23 (s, 3H) delta.

EXAMPLE 5 syn-7-[2-(2-Aminothiazol-4-yl)-2-methoxyiminoacetamido]-3-[(4-formylpyridinium methoxime)-1-ylmethyl]-3-cephem-4-carboxylate A. Preparation of 4-formylpyridine methoxime.

By following the procedures and by employing the reaction conditions and reagents used in the preparation of 4-acetylpyridine methoxime described by Example 4 part A, 10.71 g. of 4-formylpyridine was converted to the methoxime. The methoxime was obtained as an oil.

NMR (DMSO/d6): signals at 8.64 (d, 2H), 4.25 (s, 1H), 7.55 (d, 2H), and 3.92 (s, 3H) delta.

B. Preparation of title compound.

One third (6.5 ml.) of the solution of the silylated 3-iodomethyl derivative, prepared as described by Example 4 part B, was added at room temperature to a solution of 327 mg. (2.4 mmole) of the 4-formylpyridine methoxime in 1 ml. of dry acetonitrile. The mixture was stirred at room temperature for 4 hours and then chilled. The chilled mixture was treated with 234 µl. of water, the product precipitated and was separated by filtration and dried (0.91 g.).

The product was purified on C-18 silica reverse phase HPLC with acetonitrile:acetic acid:water, 20:2:78% v:v:v to provide 210 mg. of the product.

NMR (DMSO/d6-D2O): signal at 9.35 (d, 2H), 8.49 (s, 1H), 8.25 (d, 2H), 6.72 (s, 1H), 5.67, 5.64 (d, d, 2H), 5.12, 5.06 (d, d, 2H), 4.05 (s, 3H), 3.79 (s, 3H), and 3.30 (q, 2H) delta.

EXAMPLE 6 syn-7-[2-(2-Aminothiazol-4-yl)-2-methoxyiminoacetamido]-3-[(3-formylpyridinium methoxime)-1-ylmethyl]-3-cephem-4-carboxylate 3-Formylpyridine methoxime was prepared by the method described by the preceding Examples 4A and 5A.

NMR (DMSO/d6): signals at 8.92-8.44 (m, 2H), 8.27 (s, 1H), 8.00 (d, 1H), 7.44 (m, 1H), and 3.87 (s, 3H).

The methoxime 327 mg. (2.4 mmole) was reacted with one third (6.5 ml.) of the solution of the silylated 3-iodomethyl derivative prepared as described by Example 4B, and isolated and purified by HPLC by the methods described in the preceding examples.

NMR (DMSO/d6-D2O): signals at 9.49, 9.47 (bs, d, 2), 8.72 (d, 1H), 8.44 (s, 1H), 8.21 (q, 1H), 6.73 (s, 1H), 5.68, 5.67 (d, d, 2H), 5.17; 5.05 (d, d, 2H), 4.00 (s, 3H), 3.79 (s, 3H), and 3.32 (q, 2H) delta.

EXAMPLE 7 syn-7-[2-(2-Aminothiazol-4-yl)-2-methoxyiminoacetamide]-3-[(4-formylquinolinium methoxime)-1-ylmethyl]-3-cephem-4-carboxylate A. Preparation of 4-formylquinoline methoxime.

4-Formylquinoline, 10 g. (64 mmole), was added to a suspension formed with 8.3 g. (100 mmole) of methoxylamine hydrochloride and 5.4 g. (100 mmole) of sodium methylate in 100 ml. of methyl alcohol. The mixture was stirred at room temperature for 3 hours and then 100 ml. of water were added. The mixture was concentrated by evaporation and the product separated by filtration.

NMR (DMSO/d6): signal at 8.94, 8.91 (d, bs, 2H), 8.62 (d, 1H), 8.16-7.56 (m, 4H), and 4.12 (s, 3H) delta.

B. Preparation of title compound.

To a suspension of 3.64 g. of syn-7-[2-(2-aminothiazol-4-yl)-2-methoxyiminoacetamido]-3-acetoxymethyl-3-cephem-4-carboxylate in 15 ml. of chloroform were added 5 ml. of MSTFA and the mixture stirred at room temperature for one hour during which time a solution was obtained. TMSI, 3.07 ml., was added to the solution and after stirring for 15 minutes the reaction mixture was evaporated.

The residue of the silylated 3-iodomethyl derivative was dissolved in 15 ml. of dry acetonitrile and 652 µl. of THF were added.

One fourth of the solution was added to a solution of 446 mg. of the 4-formylquinoline methoxime in 2 ml. of dry acetonitrile and the mixture was stirred for 3 hours. Next, 190 µl. of water were added and the precipitated product was separated by filtration. After washing and drying the precipitate 390 mg. of crude product were obtained. The product was purified via C-18 silica reverse phase chromatography which provided 25 mg. of the purified product.

NMR (DMSO/d6-D$_2$O): signals at 9.37 (d, 1H), 9.17 (s, 1H), 9.04-8.76 (m, 2H), 8.68-7.72 (m, 3H), 6.75 (s, 1H), 5.92 (bs, 2H), 5.65 (d, 1H), 5.04 (d, 1H), 4.15 (s, 3H), and 3.81 (s, 3H) delta.

I claim:

1. A compound of the formula

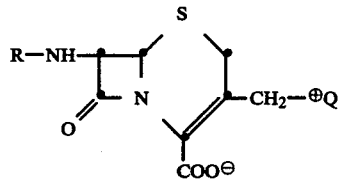

wherein
R is hydrogen, or formyl
Q is an oximino substituted pyridinium, quinolinium or isoquinolinium group of the formulas

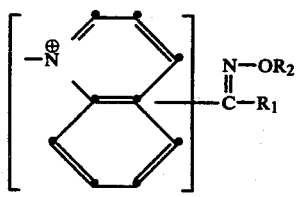

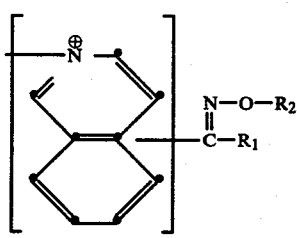

wherein
R$_1$ is hydrogen or C$_1$–C$_3$ alkyl; R$_2$ is hydrogen or C$_1$–C$_3$ alkyl; and the pharmaceutically acceptable non-toxic salts thereof.

2. The compound of claim 1 wherein R is formyl.
3. The compound of claim 2 wherein R is hydrogen.

* * * * *